United States Patent [19]

Karasawa et al.

[11] Patent Number: 5,387,715
[45] Date of Patent: Feb. 7, 1995

[54] PROCESS FOR PRODUCING α-HYDROXY-ISOBUTYRAMIDE

[75] Inventors: Minato Karasawa; Masamitsu Inomata; Hiroharu Kageyama; Kanemitsu Miyama, all of Chiba, Japan

[73] Assignee: Mitsui Toatsu Chemicals, Inc., Tokyo, Japan

[21] Appl. No.: 983,700

[22] Filed: Feb. 1, 1992

[30] Foreign Application Priority Data

Dec. 3, 1991 [JP] Japan ................... 3-319126
Dec. 3, 1991 [JP] Japan ................... 3-319127
Dec. 3, 1991 [JP] Japan ................... 3-319128

[51] Int. Cl.$^6$ ........................................... C07C 231/06
[52] U.S. Cl. ................... 564/126; 564/124; 564/128; 564/130; 564/201
[58] Field of Search .............. 564/124, 126, 201, 128, 564/130

[56] References Cited

U.S. PATENT DOCUMENTS

| | | | |
|---|---|---|---|
| 3,366,639 | 1/1968 | Haefele | 546/317 |
| 3,670,021 | 6/1972 | Goetz et al. | 564/126 |
| 3,673,250 | 6/1972 | Rauch et al. | 564/126 |
| 4,018,829 | 4/1977 | Gruber et al. | 564/126 |
| 4,222,960 | 9/1980 | Wechsberg et al. | |
| 4,987,256 | 1/1991 | Ebata et al. | 564/126 |
| 5,087,750 | 2/1992 | Uda et al. | 564/126 |

FOREIGN PATENT DOCUMENTS

| | | |
|---|---|---|
| 006140 | 1/1980 | European Pat. Off. . |
| 412310 | 2/1991 | European Pat. Off. . |
| 418512 | 3/1991 | European Pat. Off. . |
| 433611 | 6/1991 | European Pat. Off. . |
| 461850 | 12/1991 | European Pat. Off. . |
| 2131813 | 3/1972 | Germany . |
| 52-222 | 1/1977 | Japan . |
| 0093940 | 6/1982 | Japan ................... 564/126 |
| 63-57535 | 3/1988 | Japan . |
| 2-196763 | 8/1990 | Japan . |
| 3-38447 | 3/1991 | Japan . |

*Primary Examiner*—Shailendra Kumar
*Attorney, Agent, or Firm*—Burns, Doane, Swecker & Mathis

[57] ABSTRACT

Alpha-hydroxy-isobutyramide is produced by continuously hydrating acetone cyanohydrin in a liquid phase in the presence of a manganese dioxide catalyst and in the presence of a particular oxide dissolved in water, oxoacid, heteropolyacid or a salt of the acids.

23 Claims, No Drawings

PROCESS FOR PRODUCING α-HYDROXY-ISOBUTYRAMIDE

BACKGROUND OF THE INVENTION

1. Field of the Invention

The present invention relates to a process for producing α-hydroxy-isobutyramide, and more particularly, to a process for producing α-hydroxy-isobutyramide (hereinafter referred to as "HAM") by reacting continuously acetone cyanohydrin (hereinafter referred to as "ACH") with water.

2. Description of the Related Art

It is known that in general, amide compounds can be produced by the reaction of the corresponding nitrile compounds with water, and various catalysts effective for this reaction are also known.

Manganese dioxide disclosed in U.S. Pat. No. 3,366,639 is one such catalyst. Copper-containing catalysts often used for hydration of nitrile compounds are quite insufficiently effective for the hydration of α-hydroxynitrile compounds such as ACH and the like. On the contrary, manganese dioxide gives a fairly good result in the hydration of ACH as shown in West German Patent Laid-open No. 2,131,813.

Japanese Patent Application Laid-open No. Sho 52-222 (U.S. Pat. No. 4,018,829) discloses that the yield of HAM can be enhanced by adding acetone to the reaction mixture in a method for producing HAM by the hydration of ACH in the presence of manganese dioxide as a catalyst at 60°–90° C.

Japanese Patent Application Laid-open No. Sho 63-57535 discloses that fluctuation of the catalytic activity can be eliminated and the performance of the catalyst can be improved by using a manganese dioxide prepare from a heptavalent manganate and a hydrohalogenic acid.

However, according to the present inventors' investigation on Japanese Patent Application Laid-open No. Sho 52-222 (U.S. Pat. No. 4,018,829), it has been found that the catalytic activity is rapidly decreased with the lapse of time according to the industrial continuous method for producing HAM by the hydration of ACH in a solvent, i.e. an aqueous acetone, using a catalyst-suspension type reactor.

A method for solving the above-mentioned problem is shown in Japanese Patent Application Laid-open No. Hei 2-196763, that is, the decrease in the catalyst activity is suppressed by adjusting the hydrogen ion concentration (pH) of the liquid starting material mixture fed to the reactor to 4–8. However, it is not clearly explained referring to working examples whether this method can suppress the decrease in catalytic activity for a long period of time exceeding one week.

Further, in order to extend the life of manganese dioxide catalysts, Japanese Patent Application Laid-open No. Hei 3-68447 discloses an improvement in the preparation of a manganese dioxide catalyst, and U.S. Pat. No. 4,987,256 and European Patent Application Publication No. 461,850 disclose that a second component is added to manganese dioxide. These methods give some effects, but the life of the manganese dioxide thus prolonged is not always sufficient.

In view of the foregoing, when HAM is continuously produced in industry by hydrating ACH, manganese dioxide catalysts are deteriorated or deactivated resulting in frequent change of the catalysts and thereby, catalyst costs increase. Therefore, it is one of the biggest problems to maintain the activity of manganese dioxide catalysts for a long period of time.

SUMMARY OF THE INVENTION

An object of the present invention is to provide a process for producing continuously α-hydroxy-isobutyramide in which the life of manganese dioxide catalyst is long.

Another object of the present invention is to provide a process for producing continuously α-hydroxy-isobutyramide in which a regenerated manganese dioxide catalyst is effectively used.

According to one aspect of the present invention, there is provided a process for producing α-hydroxy-isobutyramide which comprises continuously hydrating acetone cyanohydrin in a liquid phase in the presence of a catalyst consisting essentially of manganese dioxide and in the presence of at least one member selected from the group consisting of (i) an oxide dissolved in water, the oxide being an oxide of an element selected from the group consisting of boron, aluminum, silicon, germanium, tin, lead, phosphorus, arsenic, antimony, vanadium, niobium, molybdenum and tungsten, (ii) an oxoacid composed of oxygen, hydrogen and the above-mentioned element, (iii) an alkali metal salt of the oxoacid, (iv) an alkaline earth metal salt of the oxoacid, (v) a heteropolyacid composed of oxygen, hydrogen and the above-mentioned elements, (vi) an alkali metal salt of the heteropolyacid, and (vii) an alkaline earth metal salt of the heteropolyacid.

According to another aspect of the present invention, there is provided the process as mentioned above in which the manganese dioxide catalyst is a regenerated manganese dioxide prepared by reducing γ-manganese (III) oxide hydrate in a deactivated state to manganese sulfate by using hydrogen peroxide and sulfuric acid and subjecting the resulting manganese sulfate to oxidation-reduction reaction under acidic conditions with sulfuric acid.

DESCRIPTION OF THE PREFERRED EMBODIMENTS

According to the present invention, the prerequisite to the hydration reaction of ACH using a manganese dioxide catalyst is to keep the starting material, ACH, stable. Otherwise, ACH is decomposed and the resulting by-product, hydrocyanic acid, polymerizes and thereby it is not possible to carry out stably the hydration of ACH, and still less the prolongation of the catalyst life.

A procedure causing to an increase in the pH value of the liquid starting material is fundamentally undesirable which is shown in prior art, for example, Japanese Patent Application Laid-open No. Hei 2-196763.

According to the present invention, for example, the pH of the liquid starting material including ACH stabilized with sulfuric acid or the like is made less than 4 so as to maintain the stability of ACH.

Although it is not desired to limit the invention to any particular theory, it is believed that in place of making a minute amount of mineral acids and hydrocyanic acid contained in the liquid starting material harmless by alkaline neutralization, the oxoacid, alkali metal salt thereof, or alkaline earth metal salt thereof added to the liquid reaction mixture preferably in a minute amount prevents catalytic poisons, mainly, hydrocyanic acid from being adsorbed on to the manganese dioxide catalyst and thereby the catalyst life is prolonged.

The manganese dioxide catalyst may be anhydrous or hydrated.

As the manganese dioxide catalyst, there may be used manganese dioxide prepared by conventional methods, for example, a method for reducing heptavalent manganese compounds in a neutral or alkaline region at 20°–100° C. [Zeit. Anorg. Allg. Chem., 309, pp. 1–32 and pp. 121–150 (1961)], a method for treating potassium permanganate and manganese sulfate in an acidic state [Biochem. J., 50, p. 43 (1951) and J. Chem. Soc., 1953, p. 2189 (1953)], a method for reducing heptavalent manganese salts with hydrohalogenic acid [Japanese Patent Application Laid-open No. Sho 63-57535], and a method of electrolytic oxidation of an aqueous manganese sulfate.

In particular, a manganese dioxide produced by the reaction of a permanganate with manganese sulfate under acidic conditions.

The catalyst is usually used as powder having an appropriate particle size.

In the present invention, water is usually used in an amount of one mole or more, preferably 2–20 moles, more preferably 4–10 moles per one mole of ACH.

As a reaction solvent, there may be used a solvent inert to the reaction other than water. For example, acetone as used in Japanese Patent Application Laid-open No. Sho 52-222 (U.S. Pat. No. 4,018,829) is preferable. The amount of acetone is usually 0.1–6.0 moles per one mole of ACH.

As a catalytic reactor used in the present invention, there may be mentioned a fixed bed type reactor or catalyst suspension type reactor. The catalyst suspension type reactor is advantageous from the standpoint of the amount of HAM production amount per unit of catalyst and unit time.

In the catalyst suspension type reactor used in the present invention, the catalyst concentration in the catalyst solution is not critical, but usually 2% by weight or more, preferably 5–50% by weight.

The feeding speed of the liquid starting material to a catalyst suspension type reactor is preferably 0.05–1.0 parts by weight of ACH per one part by weight of a catalyst and one hour.

For purposes of operating a catalyst suspension type reactor to exhibit the catalytic activity at its maximum, it is preferable to provide the outlet of a HAM producing reaction fluid from the reactor with a metal or glass filter so as to prevent the suspended catalyst of a small particle size from flowing out of the system.

The catalyst suspension type reactor may be used such that only one reactor is used to react ACH to the maximum convertion, and may be alternatively used such that two or three or more reactors are connected in series.

The reaction temperature in the present invention is usually 0°–150° C., preferably 20°–100° C. more preferably 30°–80° C. At temperatures lower than 0° C., the catalytic activity is so low that the process is not practical. On the contrary, at temperatures exceeding 150° C. the catalytic activity is high, but the yield of HAM is rapidly lowered so that the temperature range is not preferable.

According to the present invention, there are used an oxide of a particular element dissolved in water, an oxoacid containing a particular element, a heteropolyacid containing a particular element, an alkali metal salt of any of the above-mentioned acids, and an alkaline earth metal salt of any of the above-mentioned acids for the purpose of prolonging the manganese dioxide catalyst.

A center element of the oxide dissolved in water, the oxoacid and the heteropolyacid may be boron, aluminum, silicon, germanium, tin, lead, phosphorus, arsenic, antimony, vanadium, niobium, molybdenum or tungsten.

The oxide of the above-mentioned center element dissolved in water may be a hydrate of the oxide which is represented by the general formula, $$M_s^1 O_t \cdot aH_2O \tag{1}$$

where H is a hydrogen atom, O is an oxygen atom, $M^1$ is the element having a valence of m, a is a positive number larger than zero, and s and t are integers satisfying the formula, $$m \times s = 2 \times t$$

and $M^1$ is preferably aluminum, silicon, germanium, antimony, vanadium, or niobium.

The oxoacid of the present invention may be an oxoacid which is weakly or strongly acidic in the form of an aqueous solution, represented by the formula, $$H_x M_y^2 O_z \tag{2}$$

where H is a hydrogen atom, O is an oxygen atom, $M^2$ is the element having a valence of m, and x, y and z are integers satisfying the formula, $$2 \times z = m \times y + x$$

and $M^2$ is preferably boron, aluminum, silicon, germanium, tin, lead, arsenic, antimony, vanadium, niobium, molybdenum or tungsten.

The compound of formula (2) above includes a polyacid resulting from polymerization of the oxoacid of the same center element.

The heteropolyacid of the present invention may be that represented by the general formula, $$H_u M_v^3 M_w^4 O_q \tag{3}$$

where O is an oxygen atom, H is a hydrogen atom, $M^3$ is a center element having a valence of m selected from the group consisting of silicon, phosphorus, germanium and arsenic, $M^4$ is a ligand element having a valence of n selected from the group consisting of molybdenum, tungsten and vanadium, and u, v, w and q are integers satisfying the formula $$2 \times y = m \times s + n \times t + x$$

An alkali metal salt or an alkaline earth metal salt of an oxoacid or a heteropolyacid used in the present invention is in such a form that a part or all of hydrogen atoms in the formula (2) or (3) are substituted with alkali metal atom or alkaline earth metal atom.

The alkali metal salt and the alkaline earth metal salt are preferably used since the salts have an increased solubility in water.

Compounds capable of forming oxoacids such as oxoacid esters and the like in a catalytic reactor can be also used in thee present invention.

The oxide of a particular element dissolved in water used in the present invention may be represented by the general formula (1), and the oxide is present in an aqueous solution usually in the form of oxoacid as shown by the formula (2).

Therefore, it can be said that according to the present invention the catalyst life of ordinary manganese dioxide can be prolonged by the presence of oxoacid or heteropolyacid.

The function of oxoacid, heteropolyacid or salts thereof prolonging the life of manganese dioxide catalyst is mainly attributable to the anion species, and therefore, even when the hydrogen atom or atoms are replaced with a stable metal ion or ions, the resulting compound can be sufficiently used in the present invention.

As oxoacid or salts thereof, there are preferably mentioned strongly acidic oxoacids and weakly acidic oxoacids. Strongly acidic oxoacids include those of the formula (2) above where $M^2$ is arsenic, antimony, vanadium, niobium, molybdenum, or tungsten. Weakly acidic oxoacids include those of the formula (2) above where $M^2$ is boron, aluminum, silicon, germanium, tin, or lead.

As heteropolyacids, there are preferably mentioned those where the center element is silicon, phosphorus, or germanium and the ligand element is molybdenum, tungsten, or vanadium.

The amount of the oxoacid or salts thereof used in the present invention is usually 0.0001–0.50 mol per one mol of the starting material, ACH. This amount is usually 10–20000 ppm, preferably 20–15000 ppm based on the liquid reaction mixture.

When the amount is less than 0.0001 mol based on ACH or less than 10 ppm based on the liquid reaction mixture, the catalyst life is hardly prolonged. On the contrary, an amount exceeding 0.50 mol or 20000 ppm is liable to disturb the hydration activity of the manganese dioxide catalyst.

In particular, the amount of boric acid used is usually 0.001–0.50 mol, preferably 0.005–0.30 mol based on one mol of ACH, and usually 100–20000 ppm based on the liquid reaction mixture.

The amount of borate is usually 0.0001–0.10 mol, preferably 0.001–0.05 mol per one mol of ACH.

The amount of an acidic oxoacid such as silicic acid, molybdic acid, tungstic acid, metavanadic acid, and the like, a heteropolyacid such as silicotungstic acid, silicomolybdic acid, phosphomolybdic acid, and the like, or a salt of each of these acids is preferably 10–1000 ppm based on the liquid reaction mixture.

The oxoacid, alkali metal salt thereof, and/or alkaline earth metal salt thereof alone in the form of powder, preferably, an aqueous solution thereof are usually fed directly to the catalytic reactor so as to mix with the liquid reaction mixture. This method can prolong the manganese dioxide catalyst to a great extent regardless of liquid properties such as acidity and the like in an aqueous solution of the oxoacid, alkali metal salt thereof or alkaline earth metal salt thereof.

Alternatively, the oxoacid, alkali metal salt thereof or alkaline earth metal salt thereof can be added to a liquid starting material composed of ACH, acetone and water. In such case, it is necessary to pay attention to the pH of the aqueous solution in advance since the stability of ACH in the liquid starting material varies depending on the change in pH of the aqueous solution.

That is, alkali metal salts or alkaline earth metal salts of oxoacids which are acidic in an aqueous solution have generally a pH buffer action. Therefore, when such salts are added to the liquid starting material, a minute amount exhibits little effect of increasing the pH of the liquid starting material, but as the amount increases, the pH of the liquid starting material is increased, and sometimes the pH reaches the neutral region and thereby ACH become unstable. This phenomenon is the same as the procedure of neutralizing the liquid starting material with alkali as mentioned above.

As a result, the phenomenon causes the decomposition of ACH and the by-product, hydrocyanic acid polymerizes and finally it becomes inevitable to stop the hydration reaction of ACH.

Oxoacids exhibiting strong acidity in an aqueous solution, alkali metal salts thereof or alkaline earth metal salts thereof, or oxoacids exhibiting weak acidity may be fed to a catalytic reactor by various methods. For example, an aqueous solution alone of the compound may be directly fed to the catalytic reactor, or may be add to the liquid starting material. The reason why the compound can be added to the liquid starting material is that this addition cannot raise the pH though it can lower the pH, and therefore, the resulting liquid property of the liquid starting material does not make ACH instable.

As mentioned above, according to the present invention, $\alpha$-hydroxy-isobutyramide can be continuously produced in the presence of a manganese dioxide catalyst of which the hydration activity can be retained for a long period of time, for example, as long as 50 days.

However, the activity of the manganese dioxide used in the present invention for producing HAM is also lowered during the long operation time and is finally deactivated in a manner similar to other catalysts.

Heretofore there have been no report as to the deactivated state of manganese dioxide catalyst such as the structure and the physical properties of the deactivated catalyst.

The present inventors researched the regeneration of the deactivated manganese dioxide to produce the original manganese dioxide, but it was difficult to regenerate the deactivated manganese dioxide directly in the solid form. Therefore, there was a fear that disposal of the large amount of deactivated manganese dioxide might cause an environmental problem.

The present inventors have investigated the deactivated state of a manganese dioxide catalyst by means of instrumental analysis, found that most of the deactivated catalyst is in the form of $\gamma$-manganese (III) oxide hydrate, and tried to convert this compound to a useful manganese compound.

As a result, the present inventors have found that the $\gamma$-manganese (III) oxide hydrate can be converted to manganese sulfate and the resulting manganese sulfate can be converted to manganese dioxide by treating with a permanganate and thereby the manganese dioxide can be used again as a catalyst.

The deactivated manganese dioxide, i.e. $\gamma$-manganese (III) oxide hydrate, has an average valence of manganese ranging from about 3.0 to 3.5, in particular, from about 3.0 to 3.3.

According to the present invention, the deactivated manganese dioxide may be treated with hydrogen peroxide and a mineral acid.

The amount of hydrogen peroxide necessary for converting the γ-manganese (III) oxide hydrate to manganese sulfate can be calculated as follows.

The amount of γ-manganese (III) oxide hydrate where the valence of manganese is 3 and the amount of manganese dioxide where the valence of manganese is 4 are determined by means of instrumental analysis.

In the following, sulfuric acid is used as the mineral acid.

The amount of hydrogen peroxide necessary to treat the γ-manganese (III) oxide hydrate (manganese of a valence of 3) is calculated by the formula (4) below.

$$MnOOH + \tfrac{1}{2}H_2O_2 + H_2SO_4 \rightarrow MnSO_4 + 2H_2O + \tfrac{1}{2}O_2 \qquad (4)$$

The amount of hydrogen peroxide necessary to treat manganese oxide.(manganese of a valence of 4) is calculated by the formula (5) below.

$$MnO_2 + H_2O_2 + H_2SO_4 \rightarrow MnSO_4 + 2H_2O + O_2 \qquad (5)$$

The stoichiometrical amount of hydrogen peroxide is the sum of the amount of hydrogen peroxide obtained by formula (4) and that by formula (5). From a practical point of view, it is preferable to use hydrogen peroxide in somewhat of an excess amount as compared with the stoichiometric amount.

The manganese species in the γ-manganese (III) oxide hydrate is quantitatively analyzed by measuring the total amount of manganese by means of fluorescent X-ray analysis and measuring the amount of γ-manganese (III) oxide hydrate by means of X-ray diffraction using calibration curves which have been previously prepared.

The amount of divalent manganese in γ-manganese (III) oxide hydrate resulting from deactivation of manganese dioxide, for example, manganese monooxide, is negligibly small as compared with the total amount of manganese.

Therefore, the amount of tetravalent manganese dioxide (Y weight %) can be obtained by the following formula, $$Y = 1.583 \times A - 0.9875 \times B$$

where A (weight %) is the manganese content determined by fluorescent X-ray analysis and B (weight %) is the amount of γ-manganese (III) oxide hydrate determined by X-ray diffraction.

According to the present invention, the mineral acid is used for regeneration to donate the anion portion of the divalent manganese salt.

In particular, when the divalent manganese salt is reacted with a permanganate to form manganese dioxide, sulfuric acid is the most economical and can give manganese dioxide having a high activity. The amount of sulfuric acid to be used is that calculated by the abovementioned formulas (4) and (5) or more.

When the reaction to form manganese sulfate is used in liquid phase, there may be conveniently used a solvent. As the solvent, any solvent inert to the reaction may be used. For example, water is the most preferable. The concentration of the deactivated manganese dioxide in the solution is required only to be within a range enabling the stirring, and is usually 2–50%.

The reaction temperature is required to be such that the solution can be flowable, and is usually 0°–100° C., preferably 10°–50° C.

The regeneration of the deactivated manganese dioxide may be carried out, for example, as shown below.

Firstly, γ-manganese (III) oxide hydrate resulting from deactivation of manganese dioxide and a solvent are fed to a reactor and then sulfuric acid of the concentration of usually 5–50% is fed to the reactor in an amount somewhat larger than the amount of sulfuric acid corresponding to γ-manganese (III) oxide hydrate and manganese dioxide in the deactivated manganese dioxide.

Then, 5–60% (concentration) hydrogen peroxide is added to the resulting reaction mixture continuously or batchwise at a low feeding rate over 0.1–5.0 hours in an amount calculated by formulas (4) and (5) above.

After adding hydrogen peroxide, aging is effected usually for 0.5–10 hours, preferably 0.5–2 hours to convert γ-manganese (III) oxide hydrate to an aqueous solution of manganese sulfate.

Then, the resulting manganese sulfate may be reacted with a permanganate under acidic conditions with sulfuric acid according to the above-mentioned conventional method.

For example, at an elevated temperature 1 mole of manganese sulfate is reacted with 0.667 mole of a permanganate such as potassium permanganate to effect an oxidation-reduction reaction.

As mentioned above, according to the present invention, the life of an ordinary manganese dioxide catalyst can be prolonged by using oxoacid, heteropolyacid, or alkali metal salt or alkaline earth metal salt thereof in an industrial continuous production of HAM by hydration of ACH, and therefore, the production of HAM can be improved.

In addition, according to the present invention, deactivated manganese dioxide catalyst in the production of HAM which is in the form of γ-manganese (III) oxide hydrate is regenerated by converting it to manganese sulfate and treating with a permanganate, and the manganese dioxide thus regenerated is used again in the production of HAM. Therefore, environmental pollution caused by disposal of deactivated manganese dioxide can be prevented.

The invention is now more particularly described with reference to the following examples which are for the purpose of illustration only and are intended to imply no limitation thereon.

In the Examples and Comparative Examples, below, there was carried out a high load catalyst test where the amount of ACH to be supplied to the catalyst was large so as to evaluate the effect of the present invention more rapidly. In the following, "%" and "ppm" are by weight unless otherwise specified.

Preparation of Standard Catalyst (hereinafter called "STD")

Sulfuric acid was added to 2 liters of an aqueous solution of manganous sulfate (concentration: 395 g/lit.) to prepare an aqueous manganous sulfate of pH 1. Potassium permanganate (557 g) was-added to the resulting aqueous solution to effect oxidation, and then the temperature was kept at about 50° C. while one liter of water was added to the resulting slurry solution following aging for 30 min.

The slurry solution thus obtained was subjected to a sucking filtration by means of an aspirator, and the filter cake was dried in a drier at 110° C. for 12 hours to give 68 g of a catalyst of manganese dioxide.

The resulting catalyst of manganese dioxide was ground to give 520 g of the powdered catalyst of 16-100 mesh.

Preparation of ACH

In a reactor, i.e. a 2 liter round bottom-glass flask equipped with reflux condenser, stirrer, thermometer and liquid inlet portion, were placed acetone 580 g and a 2% aqueous sodium hydroxide 10 g, and then liquid hydrocyanic acid 284 g was added while keeping the temperature at 20° C.

After completion of the reaction, sulfuric acid was added to adjust the pH to 3.5, and then unreacted hydrocyanic acid and acetone were distilled off under reduced pressure to obtain 843 g of 99% ACH.

EXAMPLE 1

(Continuous Hydration Reaction, High Load Catalyst Test)

In a reactor, i.e. a 500 ml round bottom-glass flask equipped with glass stirrer, mercury thermometer, inlet for starting materials and liquid outlet with a glass ball filter, were placed 10 g of the manganese dioxide powder catalyst (STD) as obtained above and 300 g of water. The inner temperature was raised up to 60° C. and kept at this temperature.

Then, a 48.5% acetone solution of ACH prepared by using the ACH as obtained above molar ratio, ACH:acetone=1:1.6) and a 0.1% aqueous solution of boric acid were continuously fed to a catalyst-suspension type reactor at flow rates of 11.3 g/hr and 21.4 g/hr, respectively by respective quantitative pumps.

The molar ratio of ACH:acetone:water:boric acid was 1:1.6:18.5:0.0054, and the amount of boric acid was 650 ppm based on the liquid reaction mixture.

The inner temperature of the reactor was kept at 58°-62° C., and the liquid amount in the reactor was adjusted to 290-310 ml, and the operation was continued for 10 days. The change of HAM yield with time in the HAM producing reaction fluid is shown in Table 1.

COMPARATIVE EXAMPLE 1

The procedure of Example 1 was repeated except that water was used in place of the 0.1% aqueous solution of boric acid and the operation was continued for 20 days. The molar ratio of ACH: acetone: water was 1:1.6:18.5.

The change of HAM yield with time in the HAM producing reaction fluid is shown in Table 1 and Table 3.

EXAMPLE 2

The procedure of Example 1 was repeated except that a 2.0% aqueous solution of boric acid was used in place of the 0.1% aqueous solution of boric acid.

The molar ratio of ACH:acetone:water:boric acid was 1:1.6:18.1:0.108, and the amount of boric acid was 13100 ppm based on the liquid reaction mixture.

The change of HAM yield with time in the HAM producing reaction fluid is shown in Table 1.

COMPARATIVE EXAMPLE 2

The procedure of Example 2 was repeated except that the reactor was not charged with the manganese dioxide powder catalyst.

The molar ratio of ACH:acetone:water:boric acid was 1:1.6:18.1:0.108. The change of HAM yield with time in the HAM producing reaction fluid is shown in Table 1.

EXAMPLE 3

In a reactor, i.e. a 500 ml round bottom-glass flask equipped with glass stirrer, mercury thermometer, inlet for starting materials and liquid outlet with a glass ball filter, were placed 10 g of the manganese dioxide powder catalyst as obtained above and 300 g of water. The inner temperature was raised up to 60° C. and kept at this temperature.

Then, a 17.2% solution of ACH in an aqueous acetone prepared by using the ACH as obtained above (molar ratio of ACH:acetone:water=1:3.0:13) and a 0.1% aqueous solution of sodium tetraborate decahydrate (borax) were continuously fed to a catalyst-suspension type reactor at flow rates of 34.7 g/hr and 45.4 g/hr, respectively by respective quantitative pumps.

The molar ratio of ACH:acetone:water:borox was 1:3.0:48.9:0.0017, and the amount of borax was 570 ppm based on the liquid reaction mixture.

The inner temperature of the reactor was kept at 58°-62° C., and the liquid amount in the reactor was adjusted to 290-310 ml, and the operation was continued for 10 days. The change of HAM yield with time in the HAM producing reaction fluid and the pH of the reaction fluid are shown in Table 2.

COMPARATIVE EXAMPLE 3

The procedure of Example 3 was repeated except that water was used in place of the 0.1% aqueous solution of borax. The molar ratio of ACH:acetone:water was 1:3.0:48.9.

The change of HAM yield with time in the HAM producing reaction fluid and pH of the reaction fluid are shown in Table 2.

COMPARATIVE EXAMPLE 4

The procedure of Example 3 was repeated except that the reactor was not charged with the manganese dioxide powder catalyst. The molar ratio of ACH:acetone:water:borax was 1:3.0:48.9:0.0017, and the amount of borax was 570 ppm based on the liquid reaction mixture.

The change of HAM yield with time in the HAM producing reaction fluid and pH of the reaction fluid are shown in Table 2.

EXAMPLE 4

The procedure of Example 2 was repeated except that the operation was continued for 50 days.

The change of HAM yield with time in the HAM producing reaction fluid is shown in Table 3.

EXAMPLES 5-27

The procedure of Example 4 was repeated except that in place of the 2.0% aqueous solution of boric acid, there were used respective weakly acidic oxoacids in the respective amounts based on the respective liquid reaction mixtures in Table 3, respective strongly acidic oxoacids in the respective amounts based on the respective liquid reaction mixtures in Table 4, respective salts of weakly acidic oxoacids in the respective amounts based on the respective liquid reaction mixtures in Table 5, and respective salts of strongly acidic oxoacids in the respective amounts based on the respective liquid reaction mixtures in Table 6. Naturally the operation was carried out for 50 days in each case.

The respective changes of HAM yield in the HAM producing reaction fluid are shown in Tables 3-6.

In Tables 3 and 4, the listed oxides are those used for preparing the corresponding oxoacids by suspending the oxides in water, heating and dissolving them in water.

The amount of the dissolved oxoacid was determined by means of a high frequency plasma emission spectral analysis.

In Tables 3 and 4, the amount (ppm) of an oxoacid corresponding to an oxide is shown in terms of that of the oxide.

The oxoacids and salts thereof shown in Tables 3, 4 and 6 were added to the starting material, ACH.

COMPARATIVE EXAMPLES 5-15

The procedure of Comparative Example 1 was repeated except that the catalyst STD was replaced with the catalyst in each of Comparative Examples in Tables 3-6, and the life test of catalyst was carried out. The results are shown in the Tables.

In the column of catalyst, the "compound/Mn-=numerical value" stands for a manganese dioxide catalyst containing a second element which was prepared by a coprecipitating method where said compound was added to an aqueous manganese sulfate according to the STD catalyst preparation method.

The numerical value is a ratio of mole amount of said compound per total mole amount of divalent manganese and heptavalent manganese.

TABLE 1

| Operation time (day) | HAM Yield (mol. %) | | | | | Boric acid Addition (ppm) |
|---|---|---|---|---|---|---|
|  | 1 | 3 | 5 | 7 | 10 |  |
| Example 1 | 91 | 89 | 86 | 82 | 40 | 650 |
| Comparative Example 1 | 86 | 75 | 62 | 23 | 4 | 0 |
| Example 2 | 90 | 90 | 88 | 87 | 85 | 13100 |
| Comparative Example 2 | 5 | 5 | 5 | 5 | 5 | 13100 |

TABLE 2

| Operation time (day) | HAM Yield (mol. %) | | | | | Borax Addition (ppm) | pH of Liquid Product | |
|---|---|---|---|---|---|---|---|---|
|  | 1 | 3 | 5 | 7 | 10 |  | 1 | 10 |
| Example 3 | 96 | 96 | 91 | 86 | 61 | 570 | 7.7 | 7.7 |
| Comparative Example 3 | 83 | 68 | 35 | 11 | 2 | 0 | 7.3 | 4.7 |
| Comparative Example 4 | 7 | 7 | 7 | 7 | 7 | 570 | 7.1 | 7.1 |

TABLE 3

Life test of catalyst containing weakly acidic oxoacid

|  | Catalyst | Oxoacid | Amount ppm | HAM Yield (mol. %) | | | | Total productivity of catalyst g-HAM/g-Cat. |
|---|---|---|---|---|---|---|---|---|
|  |  |  |  | 1 | 10 | 30 | 50 |  |
| Comparative Example 1 | STD | None | 0 | 86 | 4 | 1 | 1 | 78 |
| Example 4 | STD | $H_3BO_3$ | 13100 | 90 | 85 | 81 | 78 | 658 |
| Example 5 | STD | $SiO_2$ | 43 | 90 | 89 | 87 | 85 | 697 |
| Example 6 | STD | $GeO_2$ | 75 | 89 | 88 | 86 | 84 | 689 |
| Example 7 | STD | $V_2O_5$ | 100 | 85 | 84 | 83 | 81 | 662 |
| Comparative Example 5 | $H_3BO_3/Mn = 0.20$ | None | 0 | 89 | 61 | 1 | 1 | 222 |
| Comparative Example 6 | $Na_2SiO_3/Mn = 0.1$ | None | 0 | 84 | 66 | 2 | 1 | 232 |
| Comparative Example 7 | $Na_2GeO_3/Mn = 0.05$ | None | 0 | 85 | 69 | 4 | 1 | 247 |

TABLE 4

Life test of catalyst containing strongly acidic oxoacid

|  | Catalyst | Oxoacid | Amount ppm | HAM Yield (mol. %) | | | | Total productivity of catalyst g-HAM/g-Cat. |
|---|---|---|---|---|---|---|---|---|
|  |  |  |  | 1 | 10 | 30 | 50 |  |
| Example 8 | STD | $Sb_2O_3$ | 200 | 84 | 82 | 80 | 76 | 639 |
| Example 9 | STD | $Nb_2O_5$ | 130 | 83 | 80 | 78 | 76 | 627 |
| Example 10 | STD | $H_2MoO_4$ | 350 | 91 | 90 | 89 | 87 | 710 |
| Example 11 | STD | $H_2WO_4$ | 360 | 87 | 84 | 83 | 83 | 667 |
| Example 12 | STD | $H_4SiW_{12}O_{40}$ | 210 | 85 | 83 | 83 | 81 | 660 |
| Example 13 | STD | $H_3PMo_{12}O_{40}$ | 200 | 84 | 81 | 80 | 80 | 643 |
| Comparative Example 8 | $H_2MoO_4/Mn = 0.05$ | None | 0 | 84 | 48 | 12 | 1 | 222 |
| Comparative Example 9 | $H_2WO_4/Mn = 0.05$ | None | 0 | 83 | 50 | 15 | 1 | 235 |
| Comparative Example 10 | $SbCl_3/Mn = 0.1$ | None | 0 | 84 | 78 | 11 | 1 | 290 |

TABLE 4

Life test of Catalyst containing weakly acidic oxoacid

|  | Catalyst | Oxoacid | Amount ppm | HAM Yield (mol. %) | | | | Total productivity of catalyst g-HAM/g-Cat. |
|---|---|---|---|---|---|---|---|---|
|  |  |  |  | 1 | 10 | 30 | 50 |  |
| Comparative Example 1 | STD | None | 0 | 86 | 4 | 1 | 1 | 78 |

TABLE 4-continued

Life test of Catalyst containing weakly acidic oxoacid

| | | | Operation time (day) | | | | Total productivity |
|---|---|---|---|---|---|---|---|
| | | Amount | HAM Yield (mol. %) | | | | of catalyst |
| | Catalyst | Oxoacid | ppm | 1 | 10 | 30 | 50 | g-HAM/g-Cat. |
| Example 14 | STD | Na$_2$B$_4$O$_7$ | 570 | 96 | 61 | 17 | 7 | 288 |
| Example 15 | STD | NaAlO$_2$ | 43 | 88 | 57 | 32 | 4 | 315 |
| Example 16 | STD | CaSiO$_3$ | 75 | 87 | 67 | 27 | 3 | 320 |
| Example 17 | STD | Na$_2$GeO$_3$ | 200 | 85 | 64 | 41 | 11 | 369 |
| Example 18 | STD | Na$_2$SnO$_3$ | 100 | 85 | 64 | 23 | 2 | 297 |
| Example 19 | STD | Na$_2$PbO$_3$ | 260 | 86 | 60 | 37 | 8 | 343 |
| Comparative Example 11 | Na$_2$SnO$_3$/Mn = 0.10 | None | 0 | 86 | 50 | 2 | 1 | 196 |
| Comparative Example 12 | Pb(NO$_3$)$_2$/Mn = 0.10 | None | 0 | 87 | 54 | 3 | 1 | 210 |
| Comparative Example 13 | Na$_2$PbO$_3$/Mn = 0.1 | None | 0 | 89 | 58 | 3 | 1 | 221 |

TABLE 6

Life test of catalyst containing strongly acidic oxoacid

| | | | Operation time (day) | | | | Total productivity |
|---|---|---|---|---|---|---|---|
| | | Amount | HAM Yield (mol. %) | | | | of catalyst |
| | Catalyst | Oxoacid | ppm | 1 | 10 | 30 | 50 | g-HAM/g-Cat. |
| Example 20 | STD | K$_2$MoO$_4$ | 510 | 85 | 84 | 82 | 81 | 659 |
| Example 21 | STD | BaWO$_4$ | 470 | 90 | 84 | 79 | 77 | 647 |
| Example 22 | STD | NaVO$_3$ | 150 | 84 | 83 | 77 | 73 | 627 |
| Example 23 | STD | NaNbO$_3$ | 200 | 86 | 85 | 84 | 82 | 670 |
| Example 24 | STD | Na$_4$SiW$_{12}$O$_{40}$ | 143 | 84 | 83 | 80 | 80 | 648 |
| Example 25 | STD | Na$_4$GeW$_{12}$O$_{40}$ | 175 | 83 | 83 | 82 | 79 | 652 |
| Example 26 | STD | Na$_3$PMo$_{12}$O$_{40}$ | 200 | 82 | 82 | 81 | 80 | 647 |
| Comparative Example 14 | K$_2$MoO$_4$/Mn = 0.05 | None | 0 | 86 | 45 | 2 | 1 | 184 |
| Comparative Example 15 | NaVO$_3$/Mn = 0.05 | None | 0 | 86 | 24 | 2 | 1 | 134 |
| Example 27 | STD | K$_2$H$_2$AsO$_4$ | 55 | 83 | 80 | 71 | 58 | 576 |

EXAMPLE 28

The catalyst life test in Example 5 was effected by extending the test time from 50 days to 70 days. The result is shown in Table 7. The catalyst was almost completely deactivated after 70 days.

The catalyst thus deactivated was filtered, washed with water, dried at 110° C. for 15 hours and subjected to X-ray diffraction analysis. It was found that the catalyst was γ-manganese (III) oxide hydrate. The composition was 95.0% of γ-manganese (III) oxide hydrate, 4.5% of manganese dioxide and 0.5% of water.

The dried catalyst, 8.0 g (manganese 90.5 mmol) was placed in a 100 ml beaker together with 35 g of water and 9.52 g (92.3 mmol) of 95% sulfuric acid, and 5.47 g (48.3 mmol) of 30% hydrogen peroxide was added to the resulting aqueous solution at room temperature with stirring over 10 min by means of a dropping funnel.

After completion of the dropping, the liquid temperature was raised to 50° C. and the reaction solution was stirred for 1 hour to give a transparent pink manganese sulfate solution free from insoluble matters.

Then, 9.65 g of potassium permanganate was added to the resulting manganese sulfate solution to oxidize and then while keeping the temperature at about 55° C., 30 ml of water was added to the slurry solution and aging was effected for 30 min.

The resulting slurry solution was filtered by suction by using an aspirator and dried at 110° C. for 12 hours by a drier to obtain 14.7 g (water content, 11%) of manganese dioxide catalyst. This manganese dioxide catalyst was ground to form powder catalyst of 16–100 mesh, and this was used as a regenerated catalyst.

The procedure of Example 5 was repeated except that the regenerated catalyst was used in place of STD catalyst, and the life of the regenerated catalyst was measured. The result is shown in Table 7. As is clear from the result, the regenerated catalyst exhibited catalytic performance similar to that of the new STD catalyst.

EXAMPLE 29

The catalyst life test in Example 10 was effected by extending the test time from 50 days to 70 days. The result is shown in Table 7. The catalyst was almost completely deactivated after 70 days.

The catalyst thus deactivated was treated in the manner similar to Example 28 and the composition of the catalyst was analyzed and found to be 77.0% of γ-manganese (III) oxide hydrate, 21.0% of manganese dioxide and 2.0% of water.

The catalyst (8.0 g) (manganese, 89.3 mmol) after drying was subjected to a regeneration treatment using 9.40 g (91.1 mmol) of 95% sulfuric acid, 6.23 g (55.4 mmol) of 30% hydrogen peroxide and 9.52 g (60.3 mmol) of potassium permanganate in a way similar to Example 28.

As a result, 14.5 g (water content, 10%) of a regenerated manganese dioxide was obtained. Then, the procedure of Example 10 was repeated except that the regenerated catalyst was used in place of STD catalyst, and a life test of the regenerated catalyst was carried out. The result is shown in Table 7. As is clear from the result, the regenerated catalyst exhibited catalytic performance similar to that of the STD catalyst.

EXAMPLE 30

The catalyst life test in Example 12 was effected by extending the test time from 50 days to 70 days. The result is shown in Table 7. The catalyst was almost completely deactivated after 70 days.

The catalyst thus deactivated was treated in a way similar to Example 28 and the composition of the catalyst was analyzed and found to be 89.0% of γ-manganese (III) oxide hydrate, 10.0% of manganese dioxide and 1.0% of water.

The catalyst (8.0 g) (manganese, 90.1 mmol) after drying was subjected to a regeneration treatment using 9.48 g (91.9 mmol) of 95% sulfuric acid, 5.74 g (50.6 mmol) of 30% hydrogen peroxide and 9.61 g (60.8 mmol) of potassium permanganate in a way similar to Example 28.

As a result, 14.6 g (water content, 10%) of a regenerated manganese dioxide catalyst was obtained.

Then, the procedure of Example 12 was repeated except that the regenerated catalyst was used in place of the STD catalyst, and the life test of the regenerated catalyst was effected. The result is shown in Table 7. As is clear from the result, the regenerated catalyst exhibited catalytic performance similar to that of the STD catalyst.

TABLE 7

Catalyst recycle test while supplying a strongly acidic oxoacid

| | | | | Operation time (day) | | | |
|---|---|---|---|---|---|---|---|
| | Catalyst | Additive to liquid reaction mixture | Amount ppm | HAM Yield (mol. %) 1 | 30 | 50 | 70 | Total productivity of catalyst g-HAM/g-Cat. |

| | Catalyst | Additive to liquid reaction mixture | Amount ppm | 1 | 30 | 50 | 70 | Total productivity of catalyst g-HAM/g-Cat. |
|---|---|---|---|---|---|---|---|---|
| Example 5 | STD | $SiO_2$ | 43 | 90 | 87 | 85 | 6 | 842 |
| Example 28 | Regenerated catalyst from Example 5 | $SiO_2$ | 43 | 90 | 87 | 84 | 6 | 839 |
| Example 10 | STD | $H_2MoO_4$ | 350 | 91 | 89 | 87 | 18 | 877 |
| Example 29 | Regenerated catalyst from Example 10 | $H_2MoO_4$ | 350 | 91 | 89 | 88 | 19 | 882 |
| Example 12 | STD | $H_4SiW_{12}O_{40}$ | 210 | 85 | 83 | 81 | 10 | 805 |
| Example 30 | Regenerated catalyst from Example 12 | $H_4SiW_{12}O_{40}$ | 210 | 85 | 83 | 82 | 12 | 811 |

What is claimed is:

1. A process for producing α-hydroxy-isobutyramide which comprises continuously hydrating acetone cyanohydrin in a liquid phase at a temperature ranging from 20° to 100° C. in the presence of a catalyst consisting essentially of manganese dioxide and in the presence of at least one member which is separate from the catalyst and which is selected from the group consisting of
   (i) an oxide dissolved in water which is a hydrate of an oxide of a member selected from the group consisting of aluminum, silicon, germanium, antimony, vanadium, and niobium,
   (ii) an oxoacid of a member selected from the group consisting of boron, aluminum, silicon, germanium, tin, arsenic, antimony, vanadium, niobium molybdenum and tungsten,
   (iii) an alkali metal salt of the oxoacid,
   (iv) an alkaline earth metal salt of the oxoacid,
   (v) a heteropolyacid of a member selected from the group consisting of silicon, phosphorous, germanium, arsenic, molybdenum, tungsten and vanadium,
   (vi) an alkali metal salt of the heteropolyacid, and
   (vii) an alkaline earth metal salt of the heteropolyacid.

2. The process according to claim 1 in which the amount of the oxoacid, heteropolyacid, or the salts thereof added to the liquid reaction mixture is 0.0001–0.50 mol. per one mol. of acetone cyanohydrin.

3. The process according to claim 1 in which the amount of the oxoacid, heteropolyacid, or the salts thereof added to the liquid reaction mixture is 10–20000 ppm.

4. The process according to claim 1 in which the oxoacid of boron is boric acid.

5. The process according to claim 4 in which the amount of boric acid added to the liquid reaction mixture is 0.001–0.50 mol. per one mol. of acetone cyanohydrin.

6. The process according to claim 4 in which the amount of boric acid added to the liquid-reaction mixture is 0.005–0.30 mol. per one mol. of acetone cyanohydrin.

7. The process according to claim 2 in which the amount of a borate added to the liquid reaction mixture is 0.0001–0.10 mol. per one mol. of acetone cyanohydrin.

8. The process according to claim 2 in which the amount of a borate added to the liquid reaction mixture is 0.001–0.05 mol. per one mol. of acetone cyanohydrin.

9. The process according to claim 1 in which the oxoacid of silicon is silicic acid.

10. The process according to claim 1 in which the oxoacid of molybenum is molybdic acid.

11. The process according to claim 1 in which the oxoacid of tungsten is tungstic acid.

12. The process according to claim 1 in which an alkali metal salt of the oxoacid of vanadium is an alkali metal salt of metavanadic acid.

13. The process according to claim 9 in which amount of silicic acid added to the liquid reaction mixture is 10–1000 ppm.

14. The process according to claim 10 in which the amount of molybdic acid added to the liquid reaction mixture is 10–1000 ppm.

15. The process according to claim 11 in which the amount of tungstic acid added to the liquid reaction mixture is 10–1000 ppm.

16. The process according to claim 12 in which the amount of the alkali metal salt of metavanadic acid added to the liquid reaction mixture is 10–1000 ppm.

17. The process according to claim 1 in which the heteropolyacid is silicotungstic acid.

18. The process according to claim 1 in which the heteropolyacid is phosphotungstic acid.

19. The process according to claim 1 in which the manganese dioxide catalyst is a regenerated manganese dioxide prepared by reducing γ-manganese (III) oxide hydrate in a deactivated state to manganese sulfate by using hydrogen peroxide and sulfuric acid and subjecting the resulting manganese sulfate to oxidation-reduction reaction under acidic conditions with sulfuric acid.

20. The process according to claim 1 in which the amount of the oxoacid, heteropolyacid, or the salts thereof added to the liquid reaction mixture is 0.0001–0.50 mol. per one mol. of acetone cyanohydrin.

21. The process according to claim 1 in which the amount of the oxoacid, heteropolyacid, or the salts thereof added to the liquid reaction mixture is 10–20000 ppm.

22. The process according to claim 1 in which the heteropolyacid is silicotungstic acid.

23. The process according to claim 1 in which the heteropolyacid is phosphotungstic acid.

* * * * *